US008524797B2

(12) United States Patent
Taniguchi et al.

(10) Patent No.: US 8,524,797 B2
(45) Date of Patent: Sep. 3, 2013

(54) WATER-ABSORBING RESIN COMPOSITION

(75) Inventors: Takayasu Taniguchi, Himeji (JP); Tatsuya Oida, Himeji (JP); Yasuhiro Nawata, Himeji (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 730 days.

(21) Appl. No.: 11/664,715

(22) PCT Filed: Oct. 24, 2005

(86) PCT No.: PCT/JP2005/019465
§ 371 (c)(1),
(2), (4) Date: Apr. 5, 2007

(87) PCT Pub. No.: WO2006/046496
PCT Pub. Date: May 4, 2006

(65) Prior Publication Data
US 2008/0071004 A1    Mar. 20, 2008

(30) Foreign Application Priority Data
Oct. 28, 2004 (JP) .................... 2004-313649

(51) Int. Cl.
*A61K 33/38* (2006.01)
*B01J 20/02* (2006.01)

(52) U.S. Cl.
USPC ............ 523/111; 424/618; 252/194; 502/402

(58) Field of Classification Search
USPC ......... 523/111; 424/618; 252/194; 502/402
See application file for complete search history.

(56) References Cited

U.S. PATENT DOCUMENTS

| 4,741,779 | A | * | 5/1988 | Mita et al. ................... 106/467 |
| 4,842,593 | A | | 6/1989 | Jordan et al. |
| 4,911,899 | A | * | 3/1990 | Hagiwara et al. ............. 423/700 |
| 6,277,772 | B1 | | 8/2001 | Gancet et al. |

(Continued)

FOREIGN PATENT DOCUMENTS

| JP | 2-84957 A | 3/1990 |
| JP | 6-271775 A | 9/1994 |

(Continued)

OTHER PUBLICATIONS

K.K. Fuji Techno System, Biryushi Kogaku Taikei-Kihon Gijutsu—(Fine Particle Engineering Major System—Fundamental Techniques-) vol. 1, Oct. 31, 2001, pp. 79-80.

(Continued)

*Primary Examiner* — Michael Pepitone
(74) *Attorney, Agent, or Firm* — Birch, Stewart, Kolasch & Birch, LLP

(57) ABSTRACT

A water-absorbent resin composition having an antimicrobial property, which suppresses the generation of dust of the antimicrobial agent. A water-absorbent resin composition comprising a water-absorbent resin and an antimicrobial agent comprising an inorganic compound carrying an antimicrobial metal, the water-absorbent resin composition being characterized in that the degree of generated dust of the water-absorbent resin composition is at most 100 CPM. The water-absorbent resin composition of the present invention can be suitably used as hygienic materials such as disposable diaper, sanitary napkin and incontinence pad; urine-absorbent materials for pets; materials for civil engineering and construction such as packing materials; drip absorbents; food freshness retaining materials such as cold-reserving agents; horticultural articles such as water-retaining materials for soils; and the like.

4 Claims, 1 Drawing Sheet

(56) References Cited

U.S. PATENT DOCUMENTS

2003/0078349 A1    4/2003  Tagawa et al.
2004/0138362 A1*   7/2004  Kim .......................... 524/403
2006/0189953 A1*   8/2006  Taniguchi et al. ........... 604/360

FOREIGN PATENT DOCUMENTS

| JP | 7-165981 A | 6/1995 |
| --- | --- | --- |
| JP | 08-092020 | 4/1996 |
| JP | 9-248454 | 9/1997 |
| JP | 2003-82250 A | 3/2003 |
| JP | 2003-165883 A | 6/2003 |
| WO | WO-01/79314 A1 | 10/2001 |
| WO | WO 2004090044 A1 * | 10/2004 |

OTHER PUBLICATIONS

Request for Inspection of File Record dated Jul. 20, 2010.
The Observation by a Third Party (with an English translation) filed in Japan on Jun. 16, 2010, in JP2006-543116.
Search Report dated Oct. 31, 2011 for corresponding European Application No. 05795594.0.

* cited by examiner

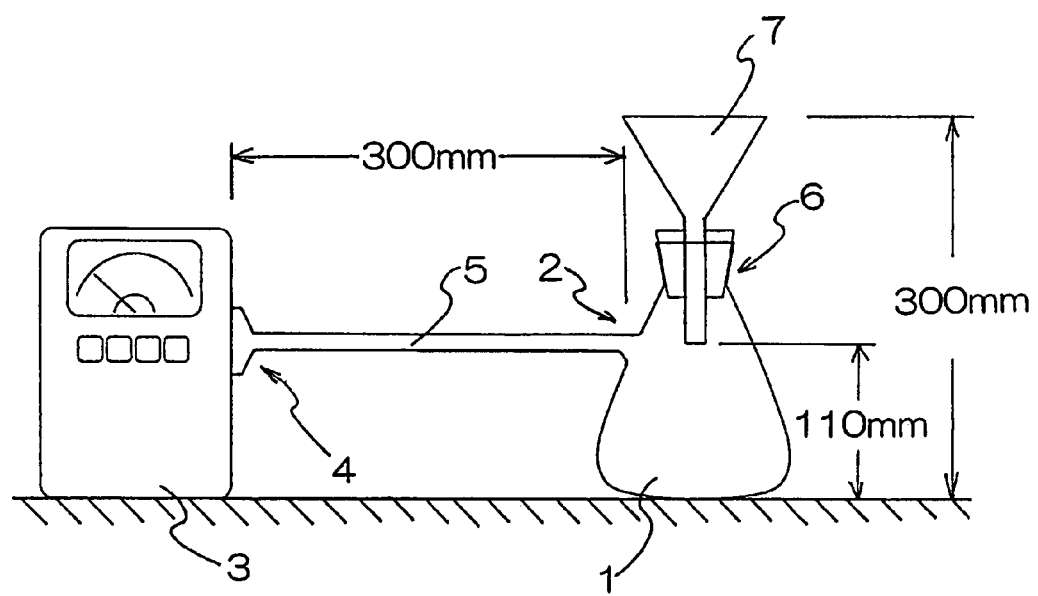

WATER-ABSORBING RESIN COMPOSITION

CROSS-REFERENCE TO RELATED APPLICATIONS

The present application is the U.S. national phase of PCT international application PCT/JP2005/019465 filed on Oct. 24, 2005, which designated the United States.

TECHNICAL FIELD

The present invention relates to a water-absorbent resin composition. More specifically, the present invention relates to a water-absorbent resin composition which can be suitably used in an absorbent article.

BACKGROUND ART

Absorbent articles have been used in various fields such as hygienic materials such as disposable diaper, sanitary napkin and incontinence pad; urine-absorbent materials for pets; materials for civil engineering and construction such as packing materials; drip absorbents; food freshness retaining materials such as cold-reserving agents; horticultural articles such as water-retaining materials for soils; and the like.

However, there are some problems in the hygienic materials such that an absorbent article which has absorbed a body fluid, especially urine, blood, sweat or the like generates an unpleasant odor. It is thought that the odor is a corruptive odor generated by degrading the components of a body fluid such as urea, protein or the like with an enzyme, which is produced by bacteria that are present on skin and in the gastrointestinal tract.

In order to suppress the generation of these odors, there has been proposed an antimicrobial high-water-absorbent resin, obtained by crosslinking copolymerization of a phosphonium salt monomer component having an antimicrobial property with a monomer component which is copolymerizable with the phosphonium salt component and capable of forming a high-water-absorbent resin after the polymerization (for example, see Patent Publication 1). However, there are some disadvantages in this antimicrobial high-water-absorbent resin, such that its monomer component having an antimicrobial property is expensive and thereby making it uneconomical.

As another means to suppress the generation of odor, there has been proposed a process comprising mixing an organic antimicrobial agent such as a quaternary nitrogen-based compound with a water-absorbent resin (for example, see Patent Publication 2). However, there is a disadvantage in this process, such that the organic antimicrobial agent used is liable to cause inflammation when the organic antimicrobial agent is contacted with skin or mucous membrane.

Therefore, in recent years, as a composition for suppressing the generation of odor, there has been proposed a composition comprising an inorganic antimicrobial agent, in which an antimicrobial metal such as silver, copper or zinc is carried on an inorganic compound, and a water-absorbent resin (for example, see Patent Publication 3). The inorganic antimicrobial agent used in this composition has high safety, and its antimicrobial strength is maintained for a long time, so that the composition is suitable for the use of a hygienic material and the like. However, there are some problems in the inorganic antimicrobial agent, such that operating environments in the production of the absorbent article are worsened, since the inorganic antimicrobial agent has poor affinity to the water-absorbent resin, and therefore the inorganic antimicrobial agent generates dust in the production of an absorbent article such as disposable diaper.

Patent Publication 1: Japanese Patent Laid-Open No. Hei 8-92020
Patent Publication 2: Japanese Patent Laid-Open No. Hei 2-1265
Patent Publication 3: Japanese Unexamined Patent Publication No. 2001-505237

DISCLOSURE OF INVENTION

Problems to be Solved by the Invention

An object of the present invention is to provide a water-absorbent resin composition having an anti-bacterial property, which suppresses the generation of dust of the anti-bacterial agent.

Means to Solve the Problems

Specifically, the present invention relates to a water-absorbent resin composition, characterized in that the water-absorbent resin composition comprises a water-absorbent resin and an anti-bacterial agent comprising an inorganic compound carrying an antimicrobial metal, wherein the degree of generated dust is at most 100 CPM.

The term "degree of generated dust" as used herein means a degree of generated dust which is determined by the following method (hereinafter the same in the present specification):

[Method for Determining Degree of Generated Dust]
(1) As shown in FIG. 1, a suction port 2 (outer diameter: 9 mm and inner inner diameter: 5 mm) provided on the side surface of a 500 mL suction filtration bottle 1 made of glass is connected to an aspiration port 4 of a digital dust meter 3 (manufactured by SHIBATA SCIENTIFIC TECHNOLOGY LTD., product number: Model P-5L) through a glass tube 5 having an inner diameter of 8 mm and a length of 300 mm.
(2) Twenty grams of a test sample is dropped into the suction filtration bottle 1 made of glass from a sample introductory port 6 provided with the upper portion of the suction filtration bottle 1 by using a powder funnel 7 (diameter: 120 mm, inner diameter of leg: 16 mm and length of leg: 70 mm).
(3) The number of powder dust being generated for a period of one minute after the completion of dropping the test sample is determined by the digital dust meter 3. The found value is referred to as a degree of generated dust (unit: CPM).

Effects of the Invention

The water-absorbent resin composition of the present invention is excellent in adhesive strength between the water-absorbent resin and the antimicrobial agent, so that the generation of dust of the antimicrobial agent can be suppressed. Therefore, the water-absorbent resin composition exhibits an effect of improving the operating environment in the production of a water-absorbent article such as disposable diaper.

BRIEF DESCRIPTION OF THE DRAWINGS

FIG. 1 A schematic explanatory view of a method for determining a degree of generated dust of the water-absorbent resin composition of the present invention.

EXPLANATION OF NUMERICAL SYMBOLS 1 a suction filtration bottle made of glass
2 suction port 3 digital dust meter
4 aspiration port
5 glass tube
6 sample introductory port
7 powder funnel

BEST MODE FOR CARRYING OUT THE INVENTION

The water-absorbent resin used in the present invention includes, for instance, crosslinked polymers of acrylic acid salt, crosslinked hydrolysates of starch-acrylic acid salt graft-copolymers, crosslinked copolymers of vinyl alcohol-acrylic acid salt, crosslinked maleic anhydride-grafted polyvinyl alcohol, crosslinked isobutylene-maleic anhydride copolymers, partially neutralized crosslinked polyacrylic acid, saponified vinyl acetate-acrylic ester copolymers, and the like. Among them, the crosslinked polymer of acrylic acid salt is preferable since the polymer is capable of absorbing water in a large amount and retaining the absorbed water in its molecule even when a certain load is applied to the polymer. The crosslinked product of the acrylic acid salt polymer is a commercially readily available compound, and preferred representative examples thereof include one manufactured by SUMITOMO SEIKA CHEMICALS CO., LTD. under the trade name of AQUA KEEP and the like.

The process for preparing a water-absorbent resin is not limited to specified one. Examples of the process include a reversed phase suspension polymerization method, an aqueous solution polymerization method and the like.

The antimicrobial agent used in the present invention comprises an inorganic compound carrying an antimicrobial metal.

The antimicrobial metal includes, for instance, silver, copper, zinc and the like. Among them, silver is preferable since silver is excellent in safety and antimicrobial property.

The inorganic compound includes, for instance, zeolite, silica gel, magnesium metasilicate aluminate, zirconium phosphate, calcium phosphate and the like. Among them, zeolite and silica gel are preferable from the viewpoint of relatively easy elution of the antimicrobial metal.

The method for preparing antimicrobial agents includes, for example, a method comprising suspending an inorganic compound in water and adding an aqueous solution of an antimicrobial metal thereto, and carrying the antimicrobial metal on the inorganic compound by such means as ion-exchange, or the like. The amount of the antimicrobial metal which is carried on the inorganic compound cannot be absolutely determined because the amount of the antimicrobial metal depends on the kinds of the antimicrobial metals and the applications of the water-absorbent resin composition of the present invention. Therefore, it is preferable that the amount of the antimicrobial metal is properly determined depending upon the applications of the water-absorbent resin composition of the present invention, and the like.

The antimicrobial agent includes an antimicrobial agent having a definite shape and an antimicrobial agent having an indefinite shape. The term "definite shape" as referred to herein means one that has a specific shape such as a spherical, rod-like, cubic, or rectangular shape. Further, the term "indefinite shape" as referred to herein means one that does not have a definite shape such as crushed, flaky or rugged shape. Among them, the indefinite shape, more preferably a rugged shape, is preferable from the viewpoint of increasing the contact area between the water-absorbent resin and the antimicrobial agent and increasing adhesion strength.

Among the antimicrobial agent having a definite shape, the antimicrobial agent having a cubic shape is preferable, from the viewpoint of increasing contact area and increasing adhesive strength. The above-mentioned cubic shape means a shape having sides each of which has approximately the same length respectively like a dice.

The antimicrobial agent having a definite shape has a median particle diameter of preferably at most 2.5 µm, more preferably 1 to 2.5 µm, even more preferably 1 to 2 µm, from the viewpoint of suppressing the generation of dust.

The antimicrobial agent having an indefinite shape has a median particle diameter of preferably at most 4 µm, more preferably 1 to 4 µm, even more preferably 1 to 3.5 µm, from the viewpoint of suppressing the generation of dust.

The median particle diameter as referred to herein is a value determined by the following method:

[Method for Determination of Median Particle Size]
(1) In a 100 mL beaker 0.3 g of an antimicrobial agent is placed, and 10 g of distilled water is introduced thereinto with mixing. Thereafter, the mixture is further sufficiently dispersed for 5 minutes with an ultrasonic cleaning machine to prepare a sample for determining a median particle size.
(2) The sample for determining a median particle size obtained is introduced into a laser diffraction/scattering particle size distribution analyzer (manufactured by Shimadzu Corporation; Model: SALD-2000J; index of refraction: 1.60-0.10i) to determine the median particle size of the antimicrobial agent.

In the present invention, as the antimicrobial agent, there can be used, for example, an antimicrobial agent which is usually commercially available, such as one manufactured by SINANEN ZEOMIC CO., LTD. under the trade name of Zeomic.

The amount of the antimicrobial agent depends upon the amount of the antimicrobial metal being carried. It is desired that the amount of the antimicrobial agent is at least 0.001 parts by weight, preferably at least 0.01 parts by weight based on 100 parts by weight of the water-absorbent resin from the viewpoint of satisfactorily exhibiting antimicrobial property, and that the amount of the antimicrobial agent is at most 1 part by weight, preferably at most 0.2 parts by weight based on 100 parts by weight of the water-absorbent resin from the viewpoint of economic advantage. From the viewpoint mentioned above, it is desired that the amount of the antimicrobial agent is 0.001 to 1 part by weight, preferably 0.01 to 0.2 parts by weight based on 100 parts by weight of the water-absorbent resin.

The water-absorbent resin composition of the present invention can be easily obtained by mixing the water-absorbent resin and the antimicrobial agent.

The method for mixing a water-absorbent resin with an antimicrobial agent includes, for example, (i) a method comprising simply powder-mixing a water-absorbent resin with an antimicrobial agent; (ii) a method comprising adding a dispersion of an antimicrobial agent to a water-absorbent resin, and thereafter drying the resulting mixture; (iii) a method comprising adding an antimicrobial agent to a water-containing gel of a water-absorbent resin and mixing them; (iv) a method comprising adding an antimicrobial agent to a water-absorbent resin during or after drying the water-absorbent resin and mixing them; and the like. However, the present invention is not limited only to those exemplified ones.

The water-absorbent resin composition of the present invention has a degree of generated dust of at most 100 CPM, preferably at most 90 CPM, more preferably at most 80 CPM, from the viewpoint of suppressing the generation of dust of the antimicrobial agent and providing an excellent working environment during the production of an absorbent article such as disposable diaper.

The degree of generated dust of the water-absorbent resin composition can be controlled to a given value by mixing an antimicrobial agent having a specified shape and a specified particle diameter with a water-absorbent resin in a given ratio in accordance with the above-mentioned method.

The water-absorbent resin composition of the present invention thus obtained can be suitably used, for example, as hygienic materials such as disposable diaper, sanitary napkin and incontinence pad; urine-absorbent materials for pets; materials for civil engineering and construction such as packing materials; drip absorbents; food freshness retaining materials such as cold-reserving agents; horticultural articles such as water-retaining materials for soils; and the like.

EXAMPLES

The present invention will be more specifically described hereinbelow by means of examples and comparative examples, without intending to limit the scope of the present invention thereto.

Example 1

The amount 100 g of a water-absorbent resin (manufactured by SUMITOMO SEIKA CHEMICALS CO., LTD. under the trade name of AQUA KEEP SA60S) and 0.1 g of a silver-zeolite-based antimicrobial agent having an indefinite shape and a median particle diameter of 3.4 μm (manufactured by SINANEN ZEOMIC CO., LTD. under the trade name of Zeomic HD10N) were sufficiently mixed with a cross rotary mixer to give 100.1 g of a water-absorbent resin composition.

Example 2

The amount 100 g of a water-absorbent resin (manufactured by SUMITOMO SEIKA CHEMICALS CO., LTD. under the trade name of AQUA KEEP SA60S) and 0.1 g of a silver-magnesium metasilicate aluminate-based antimicrobial agent having an indefinite shape and a median particle diameter of 2.3 μm (manufactured by Catalysts & Chemicals Industries Co., Ltd. under the trade name of AIS-NAZ320) were sufficiently mixed with a cross rotary mixer to give 100.1 g of a water-absorbent resin composition.

Example 3

The amount 100 g of a water-absorbent resin (manufactured by SUMITOMO SEIKA CHEMICALS CO., LTD. under the trade name of AQUA KEEP SA60S) and 0.1 g of a silver-zeolite-based antimicrobial agent having a cubic shape and a median particle diameter of 1.9 μm (manufactured by SINANEN ZEOMIC CO., LTD. under the trade name of Zeomic SJ10N) were sufficiently mixed with a cross rotary mixer to give 100.1 g of a water-absorbent resin composition.

Example 4

The amount 100 g of a water-absorbent resin (manufactured by SUMITOMO SEIKA CHEMICALS CO., LTD. under the trade name of AQUA KEEP SA60S) and 0.1 g of a silver-zeolite-based antimicrobial agent having a cubic shape and a median particle diameter of 1.4 μm (manufactured by SINANEN ZEOMIC CO., LTD. under the trade name of Zeomic SJ80N) were sufficiently mixed with a cross rotary mixer to give 100.1 g of a water-absorbent resin composition.

Example 5

The amount 100 g of a water-absorbent resin (manufactured by SUMITOMO SEIKA CHEMICALS CO., LTD. under the trade name of AQUA KEEP SA60S) and 0.1 g of a silver-zirconium phosphate-based antimicrobial agent having a cubic shape and a median particle diameter of 1.2 μm (manufactured by TOAGOSEI CO., LTD. under the trade name of NOVARON AG1100) were sufficiently mixed with a cross rotary mixer to give 100.1 g of a water-absorbent resin composition.

Comparative Example 1

The amount 100 g of a water-absorbent resin (manufactured by SUMITOMO SEIKA CHEMICALS CO., LTD. under the trade name of AQUA KEEP SA60S) and 0.1 g of a silver thiosulfate complex-silica gel-based antimicrobial agent having an indefinite shape and a median particle diameter of 4.2 μm (manufactured by Matsushita Electric Industrial Co., Ltd. under the trade name of Amenitop) were sufficiently mixed with a cross rotary mixer to give 100.1 g of a water-absorbent resin composition.

Comparative Example 2

The amount 100 g of a water-absorbent resin (manufactured by SUMITOMO SEIKA CHEMICALS CO., LTD. under the trade name of AQUA KEEP SA60S) and 0.1 g of a silver-zeolite-based antimicrobial agent having a cubic shape and a median particle diameter of 3.1 μm (manufactured by SINANEN ZEOMIC CO., LTD. under the trade name of Zeomic AJ10D) were sufficiently mixed with a cross rotary mixer to give 100.1 g of a water-absorbent resin composition.

Next, the degree of generated dust of the water-absorbent resin compositions obtained in each example and each comparative example was obtained. Also, the dust generating property when an absorbent article such as disposable diaper is produced (hereinafter simply referred to as dust generating property) is examined in accordance with the following method. The results are shown in Table 1.

[Dust Generating Property]

When an absorbent used for an absorbent article such as disposable diaper was produced by using a water-absorbent resin composition obtained in each example or each comparative example, the state of the generating dust in the course of introducing the water-absorbent resin composition into a hopper was observed with naked eyes, and evaluated on the basis of the following evaluation criteria:

[Evaluation Criteria]

○: Dust generation is hardly observed.

Δ: Dust generation is somewhat observed.

×: Dust generation is clearly observed.

TABLE 1

| | Antimicrobial Agent | | Degree of Generated Dust (CPM) | Dust Generating Property |
|---|---|---|---|---|
| | Median Particle Diameter (μm) | Shape of Particle | | |
| | Ex. No. | | | |
| 1 | 3.4 | Indefinite | 56 | ○ |
| 2 | 2.3 | Indefinite | 50 | ○ |
| 3 | 1.9 | Cubic | 75 | ○ |
| 4 | 1.4 | Cubic | 73 | ○ |
| 5 | 1.2 | Cubic | 50 | ○ |
| | Comp. Ex. No. | | | |
| 1 | 4.2 | Indefinite | 130 | X |
| 2 | 3.1 | Cubic | 209 | X |

It can be seen obviously from the results shown in Table 1 that the water-absorbent resin composition obtained in each example has a lower degree of generated dust and dust generation is less likely to take place, as compared to one obtained in each comparative example.

Industrial Applicability

The water-absorbent resin composition of the present invention can be suitably used as hygienic materials such as disposable diaper, sanitary napkin and incontinence pad; urine-absorbent materials for pets; materials for civil engineering and construction such as packing materials; drip absorbents; food freshness retaining materials such as cold-reserving agents; horticultural articles such as water-retaining materials for soils; and the like.

The invention claimed is:

1. A water-absorbent resin composition comprising a water-absorbent resin powder-mixed with 0.001 to 1 part by weight based on 100 parts by weight of said water-absorbent resin of an antimicrobial agent comprising an antimicrobial inorganic silver compound, wherein the degree of generated dust of the water-absorbent resin composition is at most 100 counts per minute ("CPM"), and wherein the antimicrobial agent has an indefinite shape and a median particle diameter of 2.3 μm to 3.5 μm.

2. The water-absorbent resin composition according to claim 1, wherein the water-absorbent resin is a member selected from the group consisting of a crosslinked polymer of an acrylic acid salt, a crosslinked hydrolysate of a starch-acrylic acid salt graft copolymer, a crosslinked copolymer of a vinyl alcohol-acrylic acid salt, a crosslinked maleic anhydride-grafted polyvinyl alcohol, a crosslinked isobutylene-maleic anhydride copolymer, a partially neutralized crosslinked polyacrylic acid, and a saponified vinyl acetate-acrylic ester copolymer.

3. The water-absorbent resin composition according to claim 1, wherein the inorganic compound is a member selected from the group consisting of zeolite, silica gel, magnesium metasilicate aluminate, zirconium phosphate, and calcium phosphate.

4. The water-absorbent resin composition according to claim 1, wherein the antimicrobial agent is a member selected from the group consisting of silver-zeolite, antimicrobial agents and silver-magnesium metasilicate aluminate antimicrobial agents.

* * * * *